(12) United States Patent
Llobregat Agusti

(10) Patent No.: US 9,272,011 B2
(45) Date of Patent: Mar. 1, 2016

(54) PHARMACEUTICAL COMPOSITION FOR TREATING URINARY INCONTINENCE AND ENURESIS

(71) Applicant: LABORATEC, S.L., Alicante (ES)

(72) Inventor: Juan Carlos Llobregat Agusti, Alicante (ES)

(73) Assignee: LABORATEC, S.L., Alicante (ES)

( * ) Notice: Subject to any disclaimer, the term of this patent is extended or adjusted under 35 U.S.C. 154(b) by 0 days.

(21) Appl. No.: 14/378,380

(22) PCT Filed: Jan. 22, 2013

(86) PCT No.: PCT/ES2013/070022
§ 371 (c)(1),
(2) Date: Aug. 13, 2014

(87) PCT Pub. No.: WO2013/121061
PCT Pub. Date: Aug. 22, 2013

(65) Prior Publication Data
US 2015/0044308 A1 Feb. 12, 2015

(30) Foreign Application Priority Data
Feb. 15, 2012 (ES) .................................. 201230242

(51) Int. Cl.
| | | |
|---|---|---|
| A61K 36/00 | (2006.01) | |
| A61K 36/185 | (2006.01) | |
| A61K 31/197 | (2006.01) | |
| A61K 31/353 | (2006.01) | |
| A61K 31/7048 | (2006.01) | |
| A61K 31/14 | (2006.01) | |
| A61K 31/355 | (2006.01) | |
| A61K 31/375 | (2006.01) | |
| A61K 31/05 | (2006.01) | |
| A61K 31/341 | (2006.01) | |
| A61K 31/352 | (2006.01) | |
| A61K 36/736 | (2006.01) | |

(52) U.S. Cl.
CPC ............... *A61K 36/185* (2013.01); *A61K 31/05* (2013.01); *A61K 31/14* (2013.01); *A61K 31/197* (2013.01); *A61K 31/341* (2013.01); *A61K 31/352* (2013.01); *A61K 31/353* (2013.01); *A61K 31/355* (2013.01); *A61K 31/375* (2013.01); *A61K 31/7048* (2013.01); *A61K 36/736* (2013.01)

(58) Field of Classification Search
None
See application file for complete search history.

(56) References Cited

U.S. PATENT DOCUMENTS

2006/0275517 A1* 12/2006 Yates ............................ 424/757

FOREIGN PATENT DOCUMENTS

| ES | 2341059 | 6/2010 |
|---|---|---|
| NZ | 526350 A * | 10/2004 |
| WO | 9209560 | 6/1992 |
| WO | 9323383 | 11/1993 |
| WO | 02085393 | 10/2002 |
| WO | 2009089442 | 7/2009 |

OTHER PUBLICATIONS

Park, Rapid in vivo screening system for anti-oxidant activity using bacterial redox sensor strains. Journal of applied microbiology, (Apr. 2010) vol. 108, No. 4, pp. 1217-1225.*

* cited by examiner

*Primary Examiner* — Qiuwen Mi
(74) *Attorney, Agent, or Firm* — Sturm & Fix LLP

(57) ABSTRACT

A pharmaceutical composition for treating urinary incontinence and/or enuresis, which comprises at least 0.5-20 wt % of a mixture of flavonoids, 2-20 wt % of condensed tannins or proantocyanidins and 0.3-60 wt % of gamma aminobutyric acid (GABA), with respect to the total composition. The composition additionally comprises at least 50% of a *Humulus lupulus* extract. The composition is used for preparing a medicine for treating incontinence and/or enuresis, in particular enuresis in children, as well as in adults or the elderly who have urine leaks such as incontinence due to stress or urgency.

9 Claims, No Drawings

PHARMACEUTICAL COMPOSITION FOR TREATING URINARY INCONTINENCE AND ENURESIS

OBJECT OF THE INVENTION

The object of the present invention is a pharmaceutical composition for treating both infantile and adult urinary incontinence as well as its use for treating said conditions.

Said composition allows enuresis in children exhibiting this urinary incontinence to be treated as well as in adults or the elderly who suffer from urinary leaks such as incontinence due to stress or urgency.

For this purpose, a pharmaceutical composition is used which comprises at least 0.5-20 wt % of a mixture of flavonoids, 2-20 wt % of condensed tannins or proantocyanidins and 0.3-60 wt % of gamma aminobutyric acid (GABA), with respect to the total composition. Said composition additionally comprises at least 50% of a *Humulus lupulus* extract.

BACKGROUND OF THE INVENTION

Urinary incontinence (UI) consists of the involuntary loss of urine at inappropriate moments and in inappropriate places and with sufficient quantity or frequency such that it presents a problem for the individual who suffers with it as well as a possible limitation on their activity and social relations. The person affected has an imperative and sudden need to urinate but is incapable of retaining the urine.

The urine leaks may be caused by involuntary situations such as sneezing, laughing, making some kind of effort or carrying out some kind of physical exercise. The loss of urine is a hygienic, social and mental problem since it influences the daily activity of the sufferer and reduces the quality of life.

It is not a disease itself, rather the consequence of an alteration in the bladder-filling phase, which is associated with numerous diseases. It may be caused by diabetes, cerebrovascular accidents, multiple sclerosis, Parkinson's disease, some surgeries or even during maternity.

Urinary incontinence, in general terms, may be:
Primary: if the child has never been able to control their losses of urine,
Secondary: if, following a period of control, they are unable to regain control,
Diurnal,
Nocturnal,
Mixed: at both times of day, and
Due to stress or effort: in adults from approximately 30 to 60 years.

Furthermore, there are a series of factors which may condition or predispose the patient to suffer from this condition like physical problems such as having a small bladder or weak musculature.

In order to control this situation, in the current prior art, various alternative palliative techniques are used such as pharmacological treatment (Hattori T., Drug treatment of urinary incontinence. Drugs of Today, 1998, 34 (2): 125-138), such as for example the commercial product, Minurin® which contains desmopressin acetate and is used for treating central insipidus diabetes and primary nocturnal enuresis in patients (children older than 5 years) with normal capacity for concentrating urine. However, these therapies usually have some secondary effects since the action mechanism of the desmopressin consists of reducing the amount of urine generated by the kidneys, which is why it is not highly advisable.

Additionally, and fundamentally in the infant population, learning techniques for control, alarm devices (the Mowrer or Pipistop® device) are also employed which are based on the detection of urine to teach the child to relate the sensation of the bladder filling with waking up.

At the same time, urinary incontinence in adults or elderly persons is also known where a loss of bladder control is produced and involves a significant psychological and social impact and may seriously affect the lifestyle of the patient.

Consequently, it is necessary in the current prior art to obtain an efficient pharmaceutical composition for treating this condition, which does not exhibit the secondary effects of the treatments of the prior art and which obtains satisfactory results in preventing infantile enuresis and both infantile and adult incontinence.

In the case of infantile enuresis, there is a need to influence what is a very frequent problem (it affects approximately 5-10% of children of 7 years of age) who regularly urinate in the bed (Bower W F, Moore K H, Shepherd R B, Adams R D. The epidemiology of childhood enuresis in Australia. Br J Urol (1996) 78:602-606) and the problem may persist into adolescence and even, occasionally, into adult life. Young boys are affected more often than young girls and there may be a familial factor. There are three pathogenic mechanisms that have sufficient scientific support to be considered, they are: nocturnal polyuria, nocturnal hyperactivity of the detrusor of the bladder and an elevated threshold to wake up. All of these may depend, in turn, on a common underlying disorder at the level of the cerebral trunk.

The first line of treatment of simple enuresis, that is to say, without underlying factors such as diabetes, kidney disease or urogenital deformations, is the enuresis alarm, which has a definitive curative potential but requires a lot of work and motivation. For this reason, there are many families who cannot adequately carry it out. In these cases, desmopressin may be the selected treatment. Desmopressin poses few risks and adverse effects, however, it may cause hyponatremia which may end up being serious if combined with an excessive intake of liquids (Robson W L, Nørgaard J P, Leung A K Hyponatremia in patients with nocturnal enuresis treated with DDAVP. Eur J Pediatr (1996) 155:959-962). For children who do not respond to the desmopressin, the anticholinergics (oxybutynin, tolterodine and propiverine) are useful as adjuvant therapies (Austin P F, Ferguson G, Yan Y, Campigotto M J, Royer M E, Copien D E. Combination therapy with desmopressin and an anticholinergic medication for nonresponders to desmopressin for monosymptomatic nocturnal enuresis: randomized, double-blind, placebo-controlled trial. Pediatrics (2008) 122:1027-1032). They are not drug which have significant toxicity, however, they may produce or aggravate constipation. Imipramine is a tricyclic anti-depressant which has been used as an antineuritic therapy. The studies present a response rate of approximately 50%. The reason for this effect is not very clear, however, the most likely reason is that it is connected to the cerebral noradrenergic action (Gepertz S, Nevéus T Imipramine for therapy resistant enuresis: a retrospective evaluation. J Urol (2004) 171:2607-2610). Imipramine is only used for treating enuresis resistant to desmopressin since the secondary effects for the most part the changes to mood may be irritating, are frequent and an overdose may pose a risk to life (Varley C K. Sudden death of a child treated with imipramine. Case study. J Child Adolesc Psychopharmachol (2000) 10:321-325).

Lastly, the modalities of alternative treatments, such as acupuncture and hypnotherapy are quite widespread. However, they do not have scientific evidence for their use in order to justify using them as a standard therapy (Glazener C M, Evans J, Cheuk D K. Complementary and miscellaneous interventions for nocturnal enuresis in children. Cochrane Datábase Syst Rev (2005) 18).

In this context, for the present invention, a pharmaceutical composition is provided based on a hops extract (*Humulus lupulus*) which comprises a therapeutically effective amount of at least gamma aminobutyric acid (GABA), flavonoids such as rutin or condensed tannins as well as other inherent components of the hops extract such as chalcones, α, humulin or lupulin acid.

DETAILED DESCRIPTION OF THE INVENTION

The present invention relates to a composition for treating infantile incontinence and adult incontinence.

Said composition has an active substance which is formed by a mixture of at least flavonoids having vasodilatory and natural antidiuretic properties (rutin), condensed tannins or proantocyanidins having astringent properties and gamma aminobutyric acid (GABA) which make use of cerebral neurotransmission and are linked to the treatment of anxiety. Said components may be obtained from vegetable extracts such as hops.

Hops (*Humulus lupulus*) is one of the three species of plant of the *Humulus* genome of the Cannabaceae family. It may be found in the wild in undergrowth, at the borders of forests or on the banks of rivers. The dark green leaves are provided with 3 to 5 jagged lobes. It has masculine and feminine flowers in different plants. The first are greenish yellow and are joined in panicles: the feminine, joined in catkins, are a clear green color. It is a lively dioecious plant which can reach up to eight meters in height. Its stalks are voluble, annual and wrap around any support.

The main active components of the plant have been isolated from the hops, which are: the flavonoids, chalcones and α acid which has a mild antibiotic effect against Gram-positive bacteria and favors the activity of malt yeast. The unfertilized female flower of the plant is used. At the base of its bracteoles, there are a number of glands which contain lupulin.

Hops has traditionally been used as a remedy for various diseases and irritations both physical as well as mental over many years; the flowers of this perennial vine plant are used for their natural sedation properties. Hops is used to alleviate occasional sleeping problems caused by nervousness and nervous tension (Lee K M, Jung K S. Song D K, Krauter M, Kim H Y. Effects of *Humulus lupulus* extract on the central nervous system in mice. Planta Med. (1993). 59 (Suppl), A691). Elevated doses of hops reduce the latency of sleep and aid the function of healthy sleep. Hops contains humulin and lupulin present in its feminine or strobile inflorescence, which cause a general state of calm without affecting attention, reflexes, or causing symptoms of addiction.

It is a plant that does not have secondary effects, or interactions with other drugs and its possible therapy uses known at the date of writing are:

Anxiolytic: GABA acts as a neurotransmitter inhibitor, having a tranquilizing effect on the central nervous system.

Sleep inducer: Its effects on insomnia could be due to the tranquilizing properties on the nervous system and the brain.

Anticonvulsant: GABA is often deficient in certain convulsive and motor disorders such as epilepsy or tardive dyskinesia.

Antihypertensive: GABA may help to regulate some cardiovascular mechanisms involved in hypertension.

Astringents: The condensed tannins have astringent properties, both for internal and topic uses. For internal use, they are used as antidiuretics, this activity being favored for a certain antiseptic effect since they precipitate the extracellular enzymes secreted by the microorganisms causing the infections, which makes them useful in infectious diarrheas.

Vasoconstrictor properties: The condensed tannins are also used both internally and topically for treating vascular conditions such as varicose veins or hemorrhoids and small wounds. In the case of topic use, they are indicated for various skin problems, being used for certain dermatoses as well as in cosmetics as astringent tonics.

Platelet antiaggregant: Rutin inhibits platelet aggregation as well as reducing the vascular permeability, making the blood thinner and improving circulation.

Additionally, the researchers of the present invention have experimentally determined that selecting various components of this medicinal species (*Humulus lupulus*), a pharmaceutical composition is obtained which is capable of palliating urinary incontinence in children as well as in adults and older people; from a pharmacological aspect, this is completely novel and inventive since it is not evident for a person skilled in the art.

The inventors of the present invention have determined the fundamental role of rutin in the pharmaceutical composition, which is the object of the present invention. Rutin is the glucoside formed between a flavonol called quercetin and a disaccharide called rutinose. Rutin is formed creating links between the disaccharide and the hydroxyl group of the quercetin. The rutin inhibits platelet aggregation as well as reducing the vascular permeability, making the blood thinner and improving circulation.

Rutin also has anti-inflammatory activity and inhibits the activity of aldose reductase, an enzyme normally present in the eye and other parts of the body. On the other hand, rutin helps to convert glucose into sorbitol, strengthens the capillaries and may reduce the symptoms of hemophilia. Moreover, it may help to prevent unpleasant edema in the legs. Rutin, as a ferulic acid, may reduce the cytotoxicity of the oxidized LDL cholesterol and reduce the risk of suffering coronary diseases. There is also some evidence that rutin may be used for treating hemorrhoids, varicose veins and microangiopathies.

On the other hand, the condensed tannins or proantocyanidins, also known as non-hydrolyzable tannins since they are only hydrolyzed with difficulty, are present in the composition, which is the object of the present invention. These types of tannins are produced during the normal metabolism of vegetables which is why they are considered physiological and are found widely distributed in the plant kingdom.

The tannins are polyphenolic compounds, generally complex, of vegetable origin, relatively elevated molecular mass, astringent taste, known and used for centuries for their property of being capable of converting skin into leather, that is to say, tanning skins. This is due to its capacity for joining with macromolecules such as carbon hydrates and proteins. They precipitate with heavy metal, protein and alkaloid salts.

These are hydrosoluble compounds, sometimes producing colloidal dissolutions in water, soluble also in alcohol and in acetone and insoluble in apolar organic dissolvents.

Of the pharmacological activities of the tannins, we may highlight their astringent properties, both for internal and topic use. For internal use, they are used as antidiuretics, this activity being favored for certain antiseptic effects since they precipitate the extracellular enzymes secreted by the microorganisms causing the infections, which makes them useful in infectious diarrheas. They also have vasoconstrictor properties which is why they are used both internally and topically for treating vascular conditions such as varicose veins or hemorrhoids and small wounds. In the case of topic use, they are indicated for various skin problems, being used for certain dermatoses as well as in cosmetics as astringent tonics.

The third essential component of the invention is gamma aminobutyric acid (GABA), main cerebral neurotransmitter inhibitor. It is derived from glutamic acid by means of decarboxylation carried out by the glutamate decarboxylase enzyme. GABA is secreted by the gabaergic cells of the spinal cord, also called interneurons; at the same time, there are many gabaergic neurons in the cerebellum, the basal ganglia and many areas of the cerebral cortex. These are mainly relevant for treating anxiety.

The GABA analogues are known as useful agents in anticonvulsive therapy for disorders of the central nervous system such as epilepsy, Huntington's disease, cerebral ischemia, Parkinson's disease, tardive dyskinesia and spasticity. It has also been suggested that the compounds may be used as antidepressive, anxiolytic and antipsychotic drugs (WO 92/09560 and WO 93/23383).

The rutin present in the composition, which is the object of the invention, may be acquired in commercial form or by chemical extraction from hops. For the rutin extraction, high polarity organic solvents such as ethanol, ethyl acetate (but with great care since it can react with certain compounds when heated) may be used. Subsequently, successive extractions may be carried out using growing polarity solvents such as: hexane/chloroform (for low polarity flavonoids). Ethyl acetate (for medium polarity flavonoids). Butynol (for high polarity flavonoids and in general those of wider pharmacological use thanks to the presence of hydroxyl and carboxyl functional groups).

The condensed tannins present in the composition, which is the object of the present invention, may be acquired in commercial form or by chemical extraction from hops. The extraction of the condensed tannins may be carried out for example in diffusion in an open tank, in an autoclave, or in a lixiviation system. Whatever the method used, the extraction results in a dark concentrated liquid with non-tannic impurities. For the filtering, the liquid is made to go through some of the canvas at pressure and when it is complete, they are cleaned by injecting hot water. The filtering process eliminates impurities and the liquid returns to be translucent, although it is still red. The following step is the discoloration by means of a chemical treatment based on sulfur dioxide (called sulfitation), or direct evaporation. Sulfitation may be carried out by two methods, called "stair" and the obsolete "cascade" method. In the "stair" method, the liquids fall from above by gravity and the $SO_2$ rises from below by diffusion. In the "cascade" method, towers, 15 to 30 meters in height filled with limestone and siliceous rocks are used. The liquid was allowed to fall through the part above and $SO_2$ was also injected via small sprinklers. Lastly, the final step of the process is the evaporation of the resulting liquid in order to concentrate the tannins.

These may be carried out in closed or open tanks (the latter is prohibited for discolored tannins because $SO_2$ is emitted into the atmosphere) which are heated using a stirrer which constantly prevents the tannin depositing on the bottom. The process is carried out until the desired concentration is obtained.

The gamma aminobutyric acid (GABA) present in the composition, which is the object of the present invention, may be acquired in commercial form or by synthesis known well by experts skilled in the art, in particular in organic chemistry.

PREFERRED EXEMPLARY EMBODIMENTS

The following specific examples are provided below to serve to illustrate the nature of the present invention. These examples are includes solely for illustrative purposes and are not to be interpreted as limitations of the invention which is claimed herein.

The children of the study group are children of 5 to 10 years (age at which complete nocturnal control of the emission of urine is common) affected by enuresis simple, that is to say, without associated disorders such as diabetes, urinary infections, urogenital or nerve deformations or constipation. A sample of 12 children per group is reckoned for this pilot study. The study is carried out in two groups: one group is administered the aromatherapy with the composition, which is the object of the invention, and the other group (placebo group) is administered solely aromatherapy, however, without the essential components of the composition, which is the object of the invention. In the study group, hops extracts are used with the following composition: sweet almond oil, tocopheryl acetate, ascorbyl palmitate, 2% essential oil of *Humulus lupulus*. Each vial contains 20 ml.

The volunteers are selected with consent from the guardians to be put forward for the study which shall be detailed below:

1. Placebo group: supply of the same compounds without the active substances of the composition, that is to say, without therapeutic effects.

2. Study group: the composition, which is the object of the invention, is supplied to this group.

The collection of data was carried out in accordance with the standards on human experimentation complying with the Nuremburg Code, the Declaration of Helsinki (1964), the Declaration of Tokyo (1975), Venice (1983), Hong Kong (1989), Sydney and supplementary directive, Directive 91/507/EC, R. D. 561/1993, Biotechnical Agreement of the Council of Europe (BOE 20-10-99) and code of ethics and professional medical standards in force.

Methodology

When the child goes to bed at night, place daily a total of 12 or 14 drops in one or two small makeup removal wipes or in cotton. The small wipes are placed on the nightstand or if this is not available, the closest possible place to the child, with the bedroom door almost closed or closed (in order to maximize its effect).

The data is collected in a diary in which the parents note the days on which the subjects have had leakage of urine during the night and the approximate amount (a lot, fair, little). The study is planned in three periods:

$1^{st}$: 7 days of baseline situation (placebo)

$2^{nd}$: 7 days with the composition, which is the object of the invention, and $3^{rd}$: 7 days following withdrawal of said composition.

A total 3 weeks of experimentation with the two groups simultaneously (the placebo and the study group) gave the following results. When the diaries of the subjects with the annotations of the incidences of urinating in the bed were received, the analysis phase began. After analyzing the 6 data groups, highly beneficial results were obtained in the case of the administration of the composition, which is the object of the present invention in comparison with the placebo; such that in the case of the placebo group, only two of the subjects stopped urinating in the bed while in the case of the study group, no less than 10 subjects controlled the enuresis over the week of treatment and 7 of them over the following week.

With the results obtained in the study group, it is observed that under baseline conditions, 100% of the subjects urinate and under conditions applying the composition, which is the object of the present invention, 20% urinate and 80% stopped urinating. Consequently, it may be concluded that the incidence of urinating in the bed decreased considerably in the study group with respect to the placebo group.

In accordance with a first important object, the present invention relates to a pharmaceutical composition for treating urinary incontinence and/or enuresis, which comprises at least 0.5-20 wt % of a mixture of flavonoids, 2-20 wt % of condensed tannins or proantocyanidins and 0.3-60 wt % of gamma aminobutyric acid (GABA), with respect to the total composition. Said composition preferably comprises at least 50% of a *Humulus lupulus* extract. The flavonoids are preferably rutin.

Specifically, the composition, which is the object of the present invention, preferably comprises choline as the acetylcholine precursor, neurotransmitter which carries out an important role in the learning and memory processes. Choline is fundamental for cardiovascular and cerebral functioning and does not only form part of the acetylcholine but also of the phosphatidylcholine. At the same time, it contributes to the development of the cellular membrane and to the displacement of lipids and nutrients between the cells.

According to another aspect, the present invention relates to a pharmaceutical composition for treating urinary incontinence and/or enuresis which comprises the following components expressed in percentages by weight, such that the individual values of the percentages of the different components of the composition are such that the total of the composition never exceeds 100%:

50-75% of *Humulus lupulus* extract,
2% of *Humulus Lupulus* essential oil extract,
20-50% of sweet almond oil,
0.1-0.5% of tocopheryl acetate, and
0.1-0.2% of ascorbyl palmitate.

According to another aspect, the composition, which is the object of the present invention, is administered in the form of an inhalable liquid, patch, tablet, capsule, injectable and/or gel.

According to another essential aspect, the composition, which is the object of the present invention, is characterized in that the dose in infant populations is 50 mg per kg of subject body weight.

According to another essential aspect, the composition, which is the object of the present invention, is characterized in that the dose in adults is between 10 and 4,000 mg per day for an adult subject.

According to another essential aspect, the composition, which is the object of the present invention, is characterized in that the dosing interval in adults is from 100 mg three times a day up to 1,000 mg four times a day.

According to another essential aspect, the present invention relates to a medicinal product for treating urinary incontinence and/or enuresis which comprises the composition, which is the object of the present invention, as well as the use of said composition for treating urinary incontinence and/or enuresis, in particular for infantile and adult enuresis and incontinence.

The invention claimed is:

1. A pharmaceutical composition for treating urinary incontinence and/or enuresis comprising 0.5-20 wt % of a mixture of flavonoids, 2-20 wt % of condensed tannins or proantocyanidins, 0.3-60 wt % of gamma aminobutyric acid (GABA), 50-75 wt % of *Humulus lupulus* extract, 20-50 wt % of sweet almond oil, 0.1-0.5 wt % of tocopheryl acetate, and 0.1-0.2 wt % of ascorbyl palmitate, with respect to the total composition.

2. The composition according to claim 1, wherein the flavonoids are rutin.

3. The composition according to claim 1, additionally comprising Vitamin E and B.

4. The composition according to claim 3, wherein the Vitamin B is choline.

5. The composition according to claim 1, wherein the pharmaceutical composition is administered in the form of an inhalable liquid, patch, tablet, capsule, injectable and/or gel.

6. The composition according to claim 1, wherein the dose in infant populations is 50 mg per kg of subject body weight.

7. The composition according to claim 1, wherein the dose in adults is between 10 mg and 4,000 mg per day for an adult subject.

8. The composition according to claim 7, wherein the dosing interval in adults is from 100 mg three times a day up to 1,000 mg four times a day.

9. A medicinal product for treating urinary incontinence and/or enuresis which comprises the composition of claim 1.

* * * * *